United States Patent [19]

Gray

[11] 3,968,105

[45] July 6, 1976

[54] PROLONGED RELEASE OF ANTIFERTILITY DRUGS

[75] Inventor: Allan Poe Gray, Chicago, Ill.

[73] Assignee: IIT Research Institute, Chicago, Ill.

[22] Filed: Dec. 30, 1974

[21] Appl. No.: 537,676

[52] U.S. Cl. .............................. 260/239.5; 424/241
[51] Int. Cl.² .......................................... C07J 43/00
[58] Field of Search ................. 260/239.5; 424/241, 424/242, 243

Primary Examiner—Elbert L. Roberts
Attorney, Agent, or Firm—Fitch, Even, Tabin & Luedeka

[57] ABSTRACT

Antifertility drug complexes which have enhanced effectiveness and prolonged release of the antifertility drug. The complex includes an antifertility drug, a polybasic acid and a polyvalent metal ion. The antifertility drug is in the form of a basic amine derivative.

11 Claims, No Drawings

PROLONGED RELEASE OF ANTIFERTILITY DRUGS

The present invention relates to antifertility drugs for use in the suppression of fertilization of female ovum. More particularly, the present invention relates to the treatment of antifertility drugs to provide long-acting forms of the drugs which may be used in a variety of ways, such as intramuscular injection and interuterine insertion.

There are many known compounds, particularly of the steroid type, which have potency as antifertility drugs. Such compounds include progesterone, norethindrone, norgestrel, norethynodrel, megestrol, chlormadinone, cyproterone, estradiol, and ethynylestradiol.

The known antifertility drugs are generally administered orally on a daily basis. The dosage of many of the known antifertility drugs is sufficient to suppress fertilization of female ovum for a period of approximately 24 hours. It has long been a goal in the administration of antifertility drugs to provide a drug which is effective for a longer period of time. Attempts have been made to increase the longevity of known antifertility drugs but such attempts have not yet proven to be effective. It would be highly desirable to provide a method for prolonging the effectiveness of known antifertility drugs and to provide antifertility drugs in a form which is effective for a prolonged period of time.

Accordingly, it is a principal object of the present invention to provide antifertility drugs in a form which is effective over a prolonged period of time.

Another object of the invention is to provide antifertility drugs having prolonged activity which are readily and easily formed into conveniently administered preparations.

A further object of the invention is to provide a method for treating antifertility drugs so as to prolong the activity of the antifertility drug after administration.

A still further object of the present invention is to provide a basic derivative of an antifertility drug having prolonged activity.

These and other objects of the present invention will become more apparent from the following detailed disclosure.

Generally, the above and other objects of the invention are achieved by treating an antifertility drug to provide a basic derivative of the drug. The basic drug is then treated with a polybasic acid and a polyvalent metal ion to form a complex. The invention applies to all known antifertility drugs of the steroid type and to all antifertility drugs having one or more free hydroxyl or keto groups. Examples of specific antifertility drugs suitable for use in the present invention are progesterone, norethindrone, norgestrel, norethynodrel, megestrol, chlormadinone, cyproterone, estradiol and ethynylestradiol.

The reaction of the antifertility drug with a polybasic acid and a polyvalent metal ion to form a complex in accordance with the present invention does not proceed until a basic derivative of the antifertility drug is formed. Each of these above described antifertility drugs are steroid compounds which have one or more hydroxy or keto groups available for reaction. In accordance with one embodiment of the present invention, a basic derivative of an antifertility drug is prepared by forming an amino ester with those drugs having a free hydroxyl group or by forming an O-amino-alkyl oxime with those drugs having a free keto group. Antifertility drugs lacking hydroxyl or keto groups may also be used. For example, those antifertility drugs which are inherently basic may be used without modification to form the complex of the invention. Other antifertility drugs may be first treated to provide functional hydroxyl or keto groups.

The basic derivatives of the antifertility drugs have the followng structure:

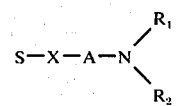

Where S is an antifertility drug nucleus; X is a labile linking group, such as ester

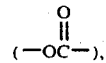

oxime (=NO—), carbamyl ester

carbonate ester

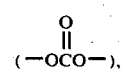

and semicarbazone

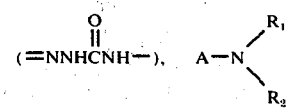

is an alkylamine wherein A is $C_1$–$C_6$ straight or branched chain alkylene; and $R_1$ and $R_2$ may be the same or different and are selected from H, $C_1$–$C_6$ straight or branched chain alkyl, $C_3$–$C_6$ cycloalkyl; $R_1$ and $R_2$ may be joined to form cycloamines selected from pyrrolidine, piperidine, morpholine and piperazine.

The labile linking groups are attached to the antifertility drug nucleus by any suitable, known technique. The alkylamine is then attached to the labile linking group by any suitable known technique. It should be understood that the labile linking group and the alkylamine maybe joined prior to attaching the labile linking group to the antifertility drug nucleus.

It should also be understood that when the antifertility drug has more than one hydroxyl or keto group, or contains a mixture of hydroxyl and keto groups that more than one labile linking group and alkylamine can be attached and that such multi-substituted antifertility drugs are suitable for use in the present invention.

In one embodiment of the invention the complex of the modified antifertility drug with the polybasic acid and the polyvalent metal ion is prepared by first stirring together an aqueous solution of a mineral acid salt of the appropriate antifertility drug or of the basic drug derivative neutralized with a mineral acid with an aqueous solution containing an equivalent amount of an alkali metal salt of the polybasic acid or an aqueous solution containing an equivalent amount of the polybasic acid neutralized with an alkali metal hydroxide. The resulting precipitate of the polybasic acid salt of the antifertility drug, after being washed with water and dried in vacuo over phosphorous pentoxide, is then treated in a stirred aqueous suspension with 0.5–2 equivalents of a 1 M solution of a water-soluble polyvalent metal salt such as zinc sulfate or aluminum nitrate, to form a complex of the antifertility drug. The complex is then washed and dried to provide the finished product.

A preferred polybasic acid is gallotannic acid, which has an approximate molecular weight of 1,700. Preferred polyvalent metal ions are zinc and aluminum.

In a preferred embodiment of the present invention the complex of the antifertility drug is prepared by combining a solution of a mineral acid salt of the antifertility drug derivative, or after the derivative is neutralized, with a mineral acid with gallotannic acid which has been pretreated with a polyvalent salt, such as zinc sulfate. In this embodiment, a stirred aqueous solution of an alkali metal salt of gallotannic acid is combined with 0.25 to 2 equivalents of a 1 M solution of a water soluble polyvalent salt, as zinc sulphate and aluminum nitrate. After about 10 minutes, 0.5 to 1 equivalent of an aqueous solution of the modified antifertility drug is added to the metal ion polybasic acid solution. After stirring the reaction mixture for 1 hour and allowing it to stand for 24 hours at room temperature, the resulting precipitate of the drug complex is collected, washed with water and dried to constant weight in vacuo over phosphorous pentoxide.

The structure of the complex of the present invention is not known. Generally, the antifertility drug comprises from about 20 to about 50 percent by weight of the complex. The polybasic acid comprises from about 45 to about 75 percent by weight and the polyvalent metal ion comprises from about 1 to about 5 percent by weight.

The antifertility drug complexes of the present invention may be administered by any suitable parenteral method. In this connection, "parenteral" is used in its broadest sense wherein it refers to materials taken into the body in a manner other than through the digestive canal. The antifertility drug complexes may be administered by intra-muscular injection, subcutaneous injection, or interuterine implacement. Other methods for administering the antifertility drug complexes include implantation of a capsule or other carrier for the antifertility drug complex.

Injectible preparations are formed by suspending the antifertility drug complex in a pharmaceutically acceptible carrier which is suitable for parenteral use. Suitable carriers include, for example, saline or a vegetable oil, such as peanut oil, corn oil, sesame oil or cotton seed oil. A particularly preferred carrier, due to its ability to further enhance the duration of action of the antifertility drug complex is an aluminum monostearate gel, comprising aluminum monostearate suspended in a suitable vegetable oil. The amount of aluminum monostearate in the gel will ordinarily be in the range of from 0.1 to 5.0 percent, preferably 1.0 to 4.0 percent by weight, based on the weight of oil. A suitable aluminum monostearate gel is prepared by slowly heating, with stirring, a mixture of 2 grams of aluminum monostearate in 100 milliliters of peanut oil to 125°C and then allowing the gel to cool to room temperature.

Injectible preparations of the antifertility drug complex are prepared by suspending the complex in a carrier in an amount equivalent to providing the drug (exclusive of the other components of the complex) in the range of from about 1 to 500 mg/ml of suspension, preferably 2 to 200 mg/ml. The suspension is then preferably mechanically worked to reduce the particle size of the suspended materials and to thoroughly disperse them in the carrier. The average particle size of the suspended materials is preferably less than 100 microns and it is particularly preferred that the average particle size be in the range of from 5 to 50 microns.

Various other ingredients commonly employed in parenteral suspensions, such as preservatives and antioxidants, may also be incorporated in the injectible preparations of the antifertility drug complexes of the present invention. Suitable preservatives include, for example, the parabens, phenol, cresol and chlorobutanol, in amounts ranging from about 0.05 to about 0.5 percent by weight, based on the weight of the suspension. Suitable antioxidants include, for example, ascorbyl palmitate, hydroquinone, propylgallate, nordihydroguaiaretic acid, butylated hydroxy toluene, butylated hydroxy anisole, alpha-tocopherol and its esters, phenyl alphanaphthylamine, lecithin, and mixtures thereof, in amounts within the range of from about 0.005 to about 0.2 percent by weight based on the weight of the suspension.

It may also be appropriate, in certain instances, to incorporate in the injectible preparations of the present invention, various other therapeutically active compounds in amounts sufficient to enhance the utility of the formulation for its intended purpose.

While not wishing to be bound by any theory, it is believed that the antifertility drug complexes of the present invention have enhanced effectiveness due to a two-stage, slow-release process. In the first stage of release, the basic amino derivative of the drug is released from the complex. In the second stage of release, metabolic conversion of the basic amino derivative of the antifertility drug is achieved by cleavage of the labile linkage of the amino group with the antifertility drug. The antifertility drug is then in a form suitable for use by the body to prevent fertilization of the ovum.

The following examples illustrate various features of the invention but are intended to in no way limit the scope of the invention which is defined in the appended claims.

EXAMPLE I

The esterification of ethynylestradiol with chloropropinonyl chloride was repeated several times under varying conditions. The most satisfactory conditions were as indicated below.

A benzene solution of ethynylestradiol (2.96 mmoles) and chloropropionyl chloride (3.36 mmoles) was heated at reflux temperature for 4 hours. The solution was concentrated to dryness and the residue was taken up in ether. The ether solution was washed with dilute alkali and water, dried, and evaporated to dryness to give 0.848 g (74% yield) of solid material. IR and tlc determinations were made which indicated that the solid material was primarily the esterified product.

The chloroester was then reacted with dimethylamine in accordance with the following:

A 2-propanol solution of the chloropropionate (1 mmole) and anhydrous dimethylamine (6 mmole) is a securely stoppered flask was allowed to stand at room temperature for 4 days. The solution was evaporated to dryness under nitrogen and the residue was taken up in ether. The ether solution was washed with water, extracted with 2% hydrochloric acid. The acid extract was made alkaline and reextracted with ether. Drying and removal of the ether and recrystallization of the residue from benzene-petroleum ether gave 50 mg (13% yield) of 3-O-(dimethylaminopropionyl) ethynylestradiol as a crystalline solid, mp 154°–155°. The ir spectrum supported the structural assignment and the purity was indicated by tlc.

EXAMPLE II

A complex of the amine ester derivative of ethynylestradiol described above was then prepared in accordance with the following procedure.

To a magnetically stirred solution at room temperature of 2.0 m equivalents (0.4 m mole) of gallotannic acid in 10 ml of 0.2 N aqueous sodium hydroxide was added 9.2 ml of an aqueous solution containing 2.2 m equivalent of zinc sulfate followed, after 10 minutes by a solution of 1.0 m equivalent of ethynylestradiol 3-(3-dimethylaminopropionate) in 11 ml of 0.1 N aqueous hydrochloric acid. Stirring was continued for 1 hour after which the reaction mixture was allowed to stand for 16 hours. The precipitate was collected, washed with distilled water and dried to constant weight in vacuo at 60°C to give 980 mg of solid material in the form of a tan powder.

To analyze for ethynylestradiol 3-(3-dimethylaminopropionate), a weighed amount of complex was dissolved in 0.1 N HCl. The solution was treated with a pH 10.4 phosphate buffer, sodium chloride was added, and the pH was adjusted to 10 with 1 N NaOH. The aqueous layer was extracted with ether and the ether extract was shaken with 0.1 N NCl. The acid was diluted to standard volume, the absorbance at 278.5 nm was determined with a Beckman Model DU-2 ultraviolet spectrophotometer, and base content was read off a standard curve. By this procedure, the ethynylestradiol 3-(3-dimethylaminopropionate) content of the complex was found to be 31.9%, which represented a 79% recovery of base in the conversion to complex.

Zinc content of the complex was determined by dissolving a weighed amount of complex in 0.1 N HCl, serially diluting the solution with 0.1 N HCl, and measuring the responses of a Jarrell-Ash Model No. 82-528 atomic absorption, flame emission spectrophotometer in comparison with the dose-response of standard zinc solutions. By this procedure the zinc content of the complex was found to be 3.6%.

The tannic acid content was calculated by difference to be 64.5%, indicating an equivalent ratio of the drug base to tannic acid of 2.1 and of zinc to tannic acid of 2.9.

EXAMPLE III

An oxime of norethindrone was prepared in accordance with the following procedure.

A solution of norethindrone; 6.5 m moles, and hydroxylamine hydrochloride, 16.4 m moles, in 10 ml of dried pyridine was stirred at room temperature for 48 hours. The progress of the reaction was followed by tlc (thin layer chromatography). The reaction mixture was then heated at 98°C. (bath temperature) for 15 minutes, allowed to cool to 55°C and the pyridine was evaporated in vacuo. The residue was extracted with ether. Drying and removal of the ether gave a residue which was recrystallized from methanol-water and methanol to yield 1.93 g (95%) of norethindrone oxime, mp 121.5°–123°C. Tlc with ethyl acetate: petroleum ether; acetone 1:1:0.2 indicated the product to be a mixture of the syn and anti isomers of the oxime.

The amine oxime derivative of norethindrone was made in accordance with the following procedure.

To an absolute ethanol solution of norethindrone oxime (1.9 m moles) and potassium methoxide (2.2 m moles) was added the 3-dimethylaminopropyl chloride obtained from 2.3 m moles of the hydrochloride salt. The reaction mixture was heated at 45° bath temperature for 16 hours, filtered, concentrated to dryness and the residue was extracted with ether. The ether solution was extracted with 2% hydrochloric acid, the acid extract was made alkaline and reextracted with ether. After drying and removal of the ether, 0.28 g of an oil residue was obtained. The oil residue was chromatographed on silica gel with 5% methanol in chloroform to give, after recrystallization from 2-propanol, 0.12 g (16%) of 3-(3-dimethylaminopropoximino)-norethindrone, mp 136°–138°C.

A complex of 3-(3-dimethylaminopropoximino) norethindrone, gallotannic acid and zinc was prepared as described in Example II.

EXAMPLE IV

An oxime of testosterone was prepared in accordance with the following procedure. A dry pyridine solution of testosterone (6.95 mmoles) and hydroxylamine hydrochloride (17.4 mmoles) was stirred at room temperature for 48 hours. The pyridine was removed in vacuo and the crystalline residue was recrystallized from methanol-water and from ethanol to yield 1.89 g (89%) of testosterone oxime, mp 207–210, indicated by tlc to be a mixture of the syn and anti oxime isomers.

The amino oxime derivative of testosterone was prepared in accordance with the following procedure.

To an absolute ethanol solution of testosterone oxime (1.96 mmoles) and potassium methoxide (2.28 mmoles) was added the 3-dimethylaminopropyl chloride obtained from 2.5 mmoles of the hydrochloride salt. After being allowed to stand 4 days at room temperature, the reaction mixture was filtered, concentrated and the residue was taken up in ether. The ether solution was extracted with 2% hydrochloric acid, the acid layer was made alkaline and shaken with ether. Drying and removal of the ether yielded 0.213 g of oil which was chromatographed on silica gel with 6% methanol in chloroform to provide after recrystallization from 2-propanol-hexane, 96 mg (12%) of 3-(3-dimethylaminopropoximino) testosterone, mp 114°–115°C.

A complex of 3-(3-dimethylaminopropoximino) testosterone, gallotannic acid and zinc was prepared as described in Example II.

What is claimed is:

1. A complex having a prolonged antifertility effect, said complex comprising the reaction product of an antifertility drug, tannic acid and a polyvalent metal ion, said antifertility drug being in the form of a basic amine derivative of said drug.

2. A complex in accordance with claim 1 wherein said polyvalent metal ion is selected from zinc and aluminum.

3. A complex in accordance with claim 1 wherein said basic amine derivative of said drug is present in said complex at a level of from about 20 to about 50 percent by weight of said complex, said polybasic acid is present at a level of from about 45 to about 75 percent by weight of said complex and said polyvalent metal ion is present at a level of from about 1 to about 5 percent by weight of said complex.

4. A complex in accordance with claim 1 wherein said antifertility drug is a steroid having at least one hydroxyl group and said basic amine derivative of said drug is an alkylamine ester.

5. A complex in accordance with claim 1 wherein said antifertility drug is a steroid having at least one keto group and said basic amine derivative is an O-aminoalkyl oxime.

6. A method for treating an antifertility drug to prolong the effect of said drug, comprising forming a basic amine derivative of said drug, providing a reaction mixture comprising said basic amine derivative, tannic acid and a polyvalent metal ion, and reacting said basic amine derivative of said drug, said polybasic acid and said polyvalent metal ion to provide a complex of said basic amine derivative of said drug, said polybasic acid and said polyvalent metal ion.

7. A method in accordance with claim 6 wherein said polyvalent metal ion is selected from zinc and aluminum.

8. A method in accordance with claim 6 wherein said basic amine derivative, said polybasic acid and said polyvalent metal ion are present in said reaction mixture at a level sufficient to provide a complex having from about 20 to about 50 percent by weight of said basic amine derivative, from about 45 to about 75 percent by weight of said polybasic acid and from 1 to about 5 percent by weight of said polyvalent metal ion.

9. A method in accordance with claim 6 wherein said basic amine derivative of said antifertility drug is an alkylamine ester.

10. A method in accordance with claim 6 wherein said basic amine derivative of said antifertility drug is an O-aminoalkyl oxime.

11. A basic amine derivative of an antifertility drug, said derivative having the formula

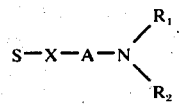

Where S is an antifertility drug nucleus; X is a labile linking group, such as ester

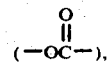

oxime (=NO—), carbamyl ester

carbonate ester

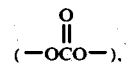

and semicarbazone

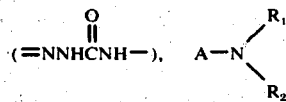

is an alkylamine wherein A is $C_1$–$C_6$ straight or branched chain alkylene; and $R_1$ and $R_2$ may be the same or different and are selected from H, $C_1$–$C_6$ straight or branched chain alkyl, $C_3$–$C_6$ cycloalkyl; $R_1$ and $R_2$ may be joined to form cycloamines selected from pyrrolidine, piperidine, morpholine and piperazine.

* * * * *